US006426353B1

(12) United States Patent
Arison et al.

(10) Patent No.: US 6,426,353 B1
(45) Date of Patent: *Jul. 30, 2002

(54) α V INTEGRIN RECEPTOR ANTAGONISTS

(75) Inventors: Byron H. Arison, Watchung, NJ (US); Donghui Cui, Newtown, PA (US); Mark E. Duggan, Schwenksville, PA (US); Wasyl Halczenko, Lansdale, PA (US); John H. Hutchinson, Philadelphia, PA (US); Thomayant Prueksaritanont, Lansdale, PA (US); Raju Subramanian, Perkasie, PA (US); Xiaojun Fang, Kalamazoo, MI (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/952,084

(22) Filed: Sep. 14, 2001

Related U.S. Application Data

(60) Provisional application No. 60/232,344, filed on Sep. 14, 2000.

(51) Int. Cl.[7] .................. A61K 31/435; C07D 471/04
(52) U.S. Cl. .......................... 514/300; 546/122
(58) Field of Search ............................ 546/122; 514/300

(56) References Cited

U.S. PATENT DOCUMENTS 6,017,926 A * 1/2000 Askew et al. ............... 514/300

FOREIGN PATENT DOCUMENTS

| WO | WO 99/30709 | 6/1999 |
|----|-------------|--------|
| WO | WO 99/30713 | 6/1999 |
| WO | WO 99/31099 | 6/1999 |
| WO | WO 00/09503 | 2/2000 |
| WO | WO 01/34602 | 5/2001 |
| WO | WO 01/38328 | 5/2001 |
| WO | WO 01/53297 | 7/2001 |

* cited by examiner

*Primary Examiner*—Bernard Dentz
(74) *Attorney, Agent, or Firm*—Philippe L. Durette; Melvin Winokur

(57) ABSTRACT

The present invention relates to novel compounds formed by metabolic conversion of compounds of structural formula (1), pharmaceutical compositions containing such compounds, and their use as αvβ3 integrin receptor antagonists. The compounds of the present invention are useful for inhibiting bone resorption, restenosis, angiogenesis, diabetic retinopathy, macular degeneration, inflammatory arthritis, cancer, and metastatic tumor growth. They are particularly useful for inhibiting bone resorption and for the treatment and prevention of osteoporosis.

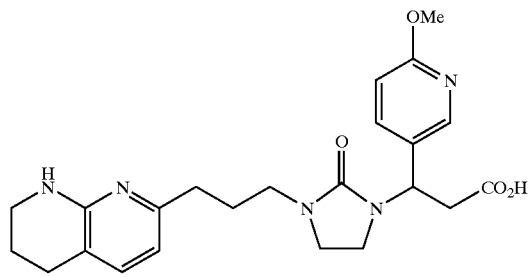

(1)

15 Claims, No Drawings

α V INTEGRIN RECEPTOR ANTAGONISTS

CROSS-REFERENCE TO RELATED APPLICATIONS

The present invention is related to U.S. provisional application Ser. No. 60/232,344, filed Sep. 14, 2000, the contents of which are hereby incorporated by reference.

BACKGROUND OF THE INVENTION

U.S. Pat. No. 6,017,926 (issued Jan. 25, 2000) discloses compounds of structural formula (1):

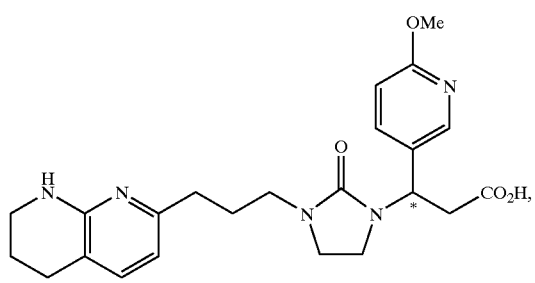

(1)

which include the two enantiomeric forms at the C-3 position (marked with *) of the propionic acid side-chain.

These compounds are antagonists of the integrin receptor αvβ3 and are therefore useful for inhibiting bone resorption, restenosis, angiogenesis, diabetic retinopathy, macular degeneration, inflammatory arthritis, cancer, and metastatic tumor growth. They are particularly useful for inhibiting bone resorption and for the treatment and prevention of osteoporosis.

SUMMARY OF THE INVENTION

The present invention relates to novel derivatives of 3-(6-methoxy-pyridin-3-yl)-3-{2-oxo-3-[3-(5,6,7,8-tetrahydro[1,8]naphthyridin-2-yl)-propyl]-imidazolidin-1-yl}-propionic acid (1), methods for their preparation, pharmaceutical compositions containing such compounds, and methods for using these compounds as αvβ3 integrin receptor antagonists. These derivatives are formed by metabolic conversion of the compounds of formula (1).

Because of their activity as αvβ3 integrin receptor antagonists, the compounds of the present invention are useful, inter alia, for inhibiting bone resorption and for the treatment and prevention of osteoporosis.

DETAILED DESCRIPTION OF THE INVENTION

In one embodiment of the present invention, there are provided compounds of structural formula (I):

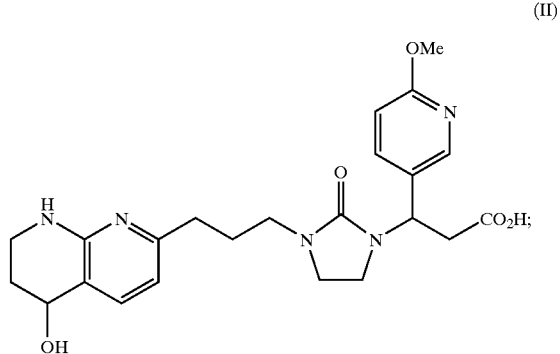

(I)

wherein at least one of $R^1$, $R^2$, and $R^3$ is hydroxy or oxo;

and the individual stereoisomers thereof, or a pharmaceutically acceptable thereof.

One class of this embodiment of the present invention is directed to compounds of structural formula (II):

(II)

and the individual stereoisomers thereof;
or a pharmaceutically acceptable salt thereof.

A subclass of this class is directed to compounds of structural formula (III):

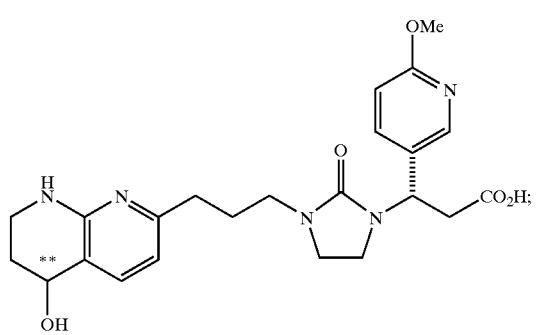

(III)

and the individual stereoisomers thereof at the hydroxylated C-5 position (marked with **) of the tetrahydro-[1,8] naphthyridine ring;

or a pharmaceutically acceptable salt thereof.

A second class of this embodiment of the present invention is directed to compounds of structural formula (IV):

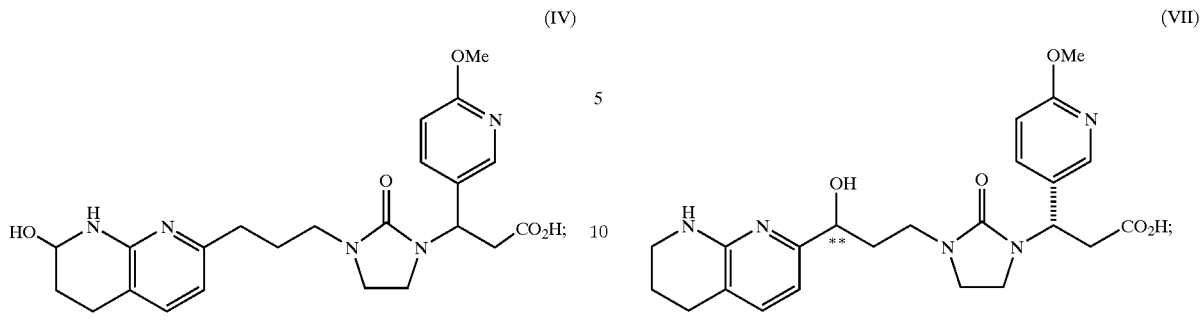

(IV)

and the individual stereoisomers thereof;

or a pharmaceutically acceptable salt thereof.

A subclass of this class is directed to compounds of structural formula (V):

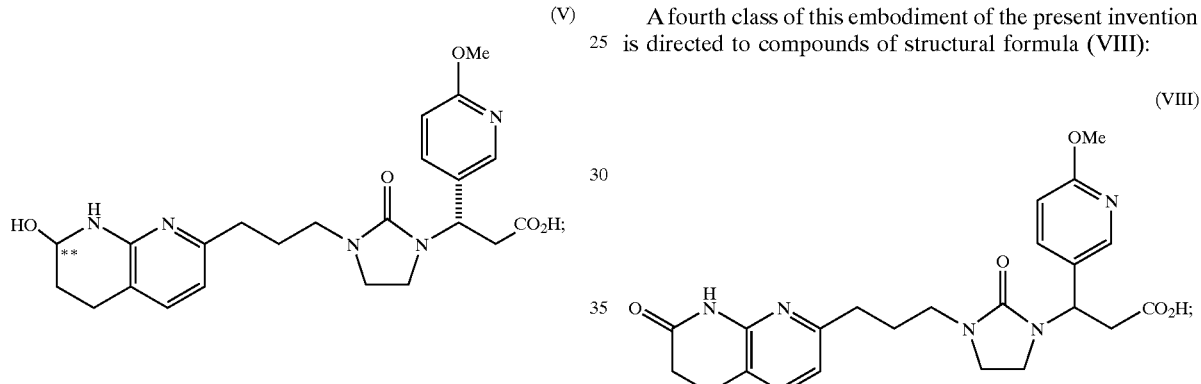

(V)

and the individual stereoisomers thereof at the hydroxylated C-7 position (marked with **) of the tetrahydro-[1,8]naphthyridine ring;

or a pharmaceutically acceptable salt thereof.

A third class of this embodiment of the present invention is directed to compounds of structural formula (VI):

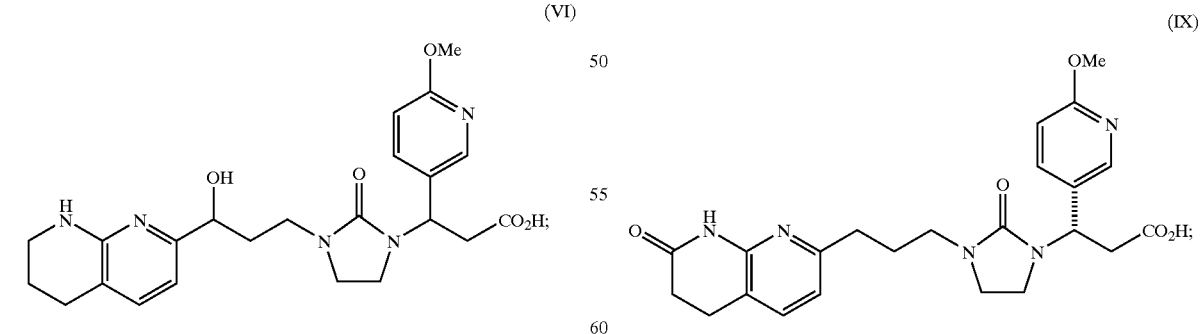

(VI)

and the individual stereoisomers thereof; or a pharmaceutically acceptable salt thereof.

A subclass of this class of this is directed to compounds of structural formula (VII):

(VII)

and the individual stereoisomers thereof at the hydroxylated benzylic position (marked with **) of the tetrahydro-[1,8]naphthyridine ring;

or a pharmaceutically acceptable salt thereof.

A fourth class of this embodiment of the present invention is directed to compounds of structural formula (VIII):

(VIII)

and the individual stereoisomers thereof; or a pharmaceutically acceptable salt thereof.

A subclass of this class is directed to the compound of structural formula (IX):

(IX)

or a pharmaceutically acceptable salt thereof.

A second embodiment of the present invention is directed to compounds of structural formula (X):

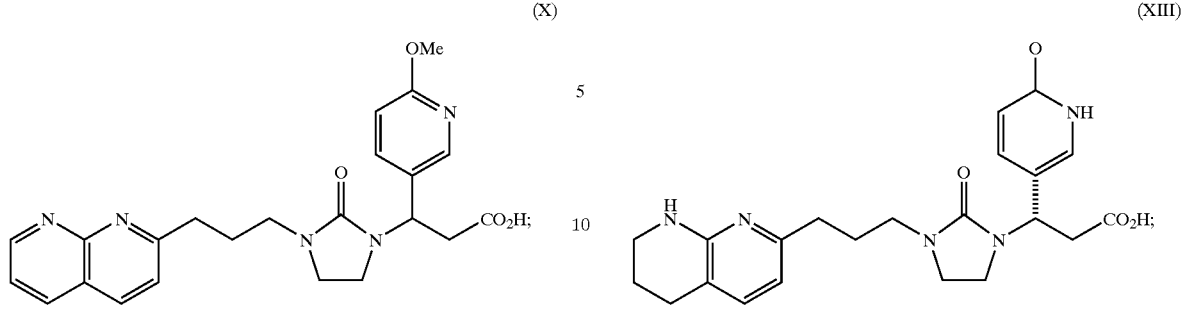

(X)

and the individual stereoisomers thereof; or a pharmaceutically acceptable salt thereof.

A class of this embodiment is directed to the compound of structural formula (XI):

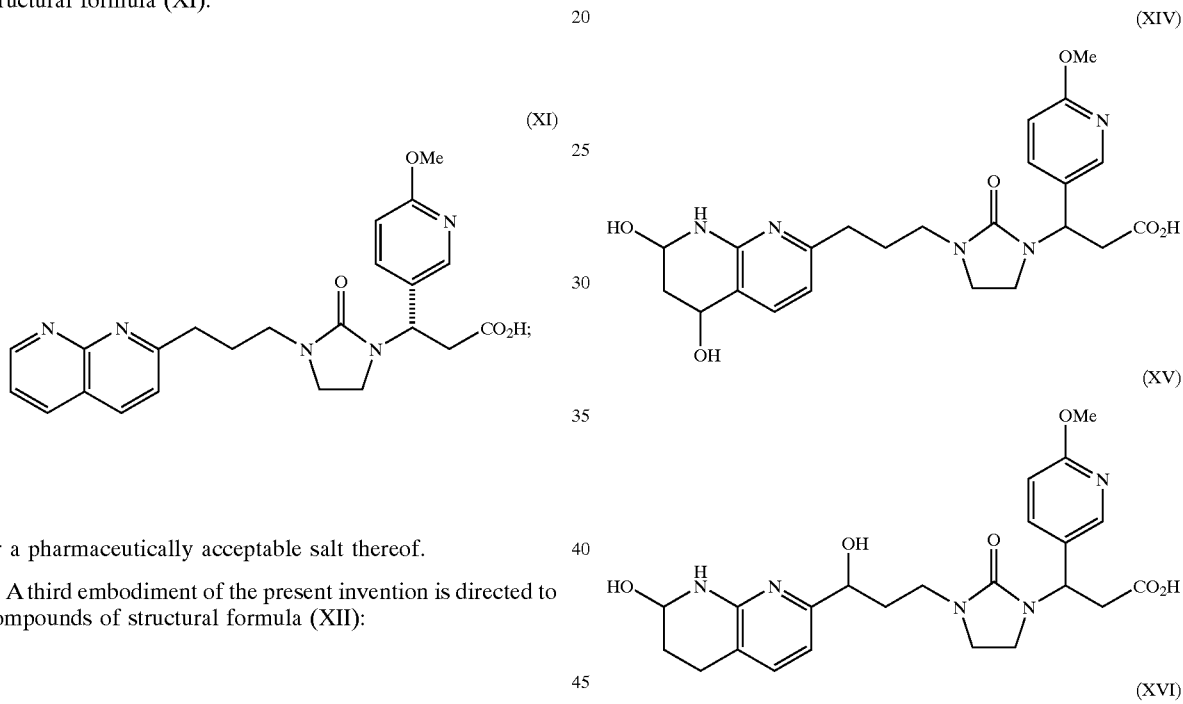

(XI)

or a pharmaceutically acceptable salt thereof.

A third embodiment of the present invention is directed to compounds of structural formula (XII):

(XII)

and the individual stereoisomers thereof; or a pharmaceutically acceptable salt thereof.

A class of this embodiment is directed to the compound of structural formula (XII):

(XIII)

or a pharmaceutically acceptable salt thereof.

In a further embodiment of the compounds of the present invention, there are provided bis-hydroxylated derivatives of structural formulae XIV–XVI:

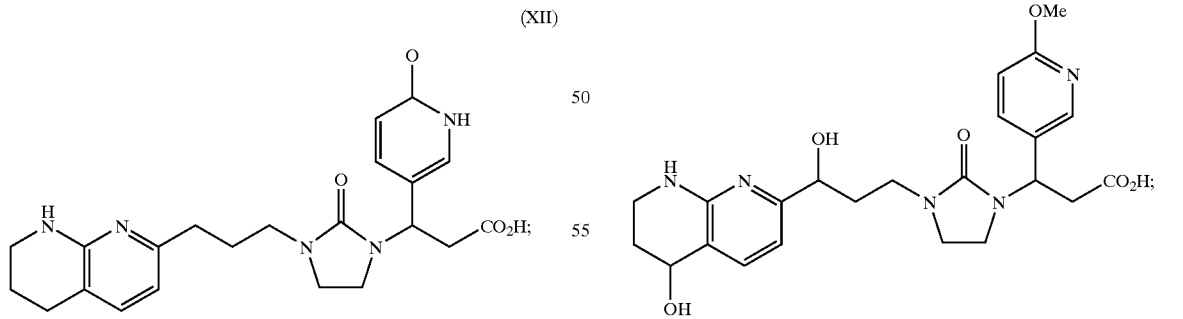

(XIV)

(XV)

(XVI)

and the individual stereoisomers thereof,
or a pharmaceutically acceptable salt thereof.

For use in medicine, the salts of the compounds of this invention refer to non-toxic "pharmaceutically acceptable salts." Other salts may, however, be useful in the preparation of the compounds according to the invention or of their pharmaceutically acceptable salts. Salts of basic compounds encompassed within the term "pharmaceutically acceptable salts" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The compounds of the present invention can have chiral centers and can thus occur as racemates, racemic mixtures, single enantiomers, diastereomeric mixtures, and individual diastereomers, with all isomeric forms being included in the present invention. Therefore, where a compound is chiral, the separate enantiomers or diastereomers, substantially free of the other, are included within the scope of the invention; further included are all mixtures of the two enantiomers.

Compounds of the present invention may be separated into enantiomeric pairs of diastereoisomers by, for example, fractional crystallization from a suitable solvent, for example, methanol or ethyl acetate or a mixture thereof. The pair of enantiomers (racemic mixture) thus obtained may be resolved into single enantiomers by conventional means, for example, by the use of an optically active acid as a resolving agent, or by HPLC using a chiral stationary phase. Alternatively, any stereoisomer of a compound of the present invention may be obtained by stereospecific synthesis using optically pure starting materials or reagents of known configuration.

Also included within the scope of the invention are polymorphs and hydrates of the compounds of the instant invention.

The term "therapeutically effective amount" shall mean that amount of a drug or pharmaceutical agent that will elicit the biological or medical response of a tissue, system, animal or human that is being sought by a researcher or clinician.

The term "integrin receptor antagonist," as used herein, refers to a compound which binds to and antagonizes the $\alpha v \beta 3$ receptor.

The term "bone resorption," as used herein, refers to the process by which osteoclasts degrade bone.

Compounds of the present invention display an affinity for the $\alpha v \beta 3$ integrin receptor of less than 100 nanomolar. Compounds of this invention are therefore useful for treating mammals suffering from a bone condition caused or mediated by increased bone resorption, who are in need of such therapy. Pharmacologically effective amounts of the compounds, including pharmaceutically acceptable salts thereof, are administered to the mammal, to inhibit the activity of mammalian osteoclasts.

The compounds of the present invention are administered in dosages effective to antagonize the $\alpha v \beta 3$ receptor where such treatment is needed, as, for example, in the prevention or treatment of osteoporosis.

Illustrating the invention is the method for eliciting an $\alpha v \beta 3$ antagonizing effect. More particularly, the $\alpha v \beta 3$ antagonizing effect is selected from inhibition of: bone resorption, restenosis, angiogenesis, diabetic retinopathy, macular degeneration, inflammatory arthritis, cancer, and metastatic tumor growth. In one embodiment of the method, the $\alpha v \beta 3$ antagonizing effect is the inhibition of bone resorption.

More particularly illustrating the invention is a pharmaceutical composition comprising any of the compounds described above and a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Further illustrating the invention is a method of treating and/or preventing a condition mediated by antagonism of the $\alpha v \beta 3$ integrin receptor in a mammal in need thereof, comprising administering to the mammal a therapeutically effective amount of any of the compounds described above. Preferably, the condition is selected from bone resorption, osteoporosis, restenosis, diabetic retinopathy, macular degeneration, angiogenesis, atherosclerosis, inflammatory arthritis, cancer, and metastatic tumor growth. More preferably, the condition is selected from osteoporosis and cancer. Most preferably, the condition is osteoporosis.

More specifically exemplifying the invention is a method of eliciting an $\alpha v \beta 3$ integrin antagonizing effect in a mammal in need thereof, comprising administering to the mammal a therapeutically effective amount of any of the compounds or any of the pharmaceutical compositions described above. Preferably, the $\alpha v \beta 3$ antagonizing effect is selected from inhibition of bone resorption, inhibition of restenosis, inhibition of atherosclerosis, inhibition of angiogenesis, inhibition of diabetic retinopathy, inhibition of macular degeneration, inhibition of inflammatory arthritis, or inhibition of cancer or metastatic tumor growth. More preferably, the $\alpha v \beta 3$ antagonizing effect is inhibition of bone resorption.

Additional examples of the invention are methods of inhibiting bone resorption and of treating and/or preventing osteoporosis in a mammal in need thereof, comprising administering to the mammal a therapeutically effective amount of any of the compounds or any of the pharmaceutical compositions decribed above.

Additional illustrations of the invention are methods of treating hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment in a mammal in need thereof, comprising administering to the mammal a therapeutically effective amount of any of the compounds or any of the pharmaceutical compositions described above.

More particularly exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of bone resorption, cancer, metastatic tumor growth, restenosis, atherosclerosis, diabetic retinopathy, macular degeneration, inflammatory arthritis, and/or angiogenesis.

Also exemplifying the invention are compositions further comprising an active ingredient selected from the group consisting of a) an organic bisphosphonate or a pharmaceutically acceptable salt or ester thereof,
b) an estrogen receptor modulator,
c) an androgen receptor modulator,
d) a cytotoxic/antiproliferative agent,
e) a matrix metalloproteinase inhibitor,
f) an inhibitor of epidermal-derived, fibroblast-derived, or platelet-derived growth factors,
g) an inhibitor of VEGF,
h) an antibody to a growth factor or to a growth factor receptor,
i) an inhibitor of Flk-1/KDR, Flt-1, Tck/Tie-2, or Tie-1,
j) a cathepsin K inhibitor,
k) a growth hormone secretagogue,
l) an inhibitor of osteoclast proton ATPase,
m) an inhibitor of urokinase plasminogen activator (u-PA),
n) a tumor-specific antibody-interleukin-2 fusion protein,
o) an inhibitor of HMG-CoA reductase, and
p) a prenylation inhibitor, such as a farnesyl transferase inhibitor or a geranylgeranyl transferase inhibitor or a dual farnesyl/geranylgeranyl transferase inhibitor; and mixtures thereof.

(See, B. Millauer et al., "Dominant-Negative Inhibition of Flk-1 Suppresses the Growth of Many Tumor Types in Vivo", *Cancer Research*, 56, 1615–1620 (1996), which is incorporated by reference herein in its entirety).

Preferably, the active ingredient is selected from the group consisting of:

a) an organic bisphosphonate or a pharmaceutically acceptable salt or ester thereof,
b) an estrogen receptor modulator,
c) an androgen receptor modulator,
d) an inhibitor of osteoclast proton ATPase,
e) an inhibitor of HMG-CoA reductase, and
f) a cathepsin K inhibitor; and mixtures thereof.

Nonlimiting examples of such bisphosphonates include alendronate, etidronate, pamidronate, risedronate, ibandronate, and pharmaceutically acceptable salts and esters thereof. A particularly preferred bisphosphonate is alendronate, especially alendronate monosodium trihydrate.

Nonlimiting examples of estrogen receptor modulators include estrogen, progesterin, estradiol, droloxifene, raloxifene, and tamoxifene.

Nonlimiting examples of cytotoxic/antiproliferative agents are taxol, vincristine, vinblastine, and doxorubicin.

Cathepsin K, formerly known as cathepsin O2, is a cysteine protease and is described in PCT International Application Publication No. WO 96/13523, published May 9, 1996; U.S. Pat. No. 5,501,969, issued Mar. 3, 1996; and U.S. Pat. No. 5,736,357, issued Apr. 7, 1998, all of which are incorporated by reference herein in their entirety. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis.

Members of the class of HMG-CoA reductase inhibitors, known as the "statins," have been found to trigger the growth of new bone, replacing bone mass lost as a result of osteoporosis (see The Wall Street Journal, Friday, Dec. 3, 1999, page B1). Therefore, the statins hold promise for the treatment of bone resorption. Nonlimiting examples of statins are lovastatin, simvastatin, atorvastatin, and pravastatin.

Evidence for crucial role of the urokinase-urokinase receptor (u-PA-u-PAR) in angiogenesis, tumor invasion, inflammation, and matrix remodeling during wound healing and development has been presented [see Y. Koshelnick et al., "Mechanisms of signaling through Urokinase Receptor and the Cellular Response," *Thrombosis and Haemostasis* 82: 305–311 (1999) and F. Blasi, "Proteolysis, Cell Adhesion, Chemotaxis, and Invasiveness Are Regulated by the u-PA-u-PAR-PAI-1 System," *Thrombosis and Haemostasis* 82: 298–304 (1999)]. Thus, specific antagonists of the binding of u-PA to u-PAR have been found to inhibit cell-surface plasminogen activation, tumor growth, and angiogenesis in both in vitro and in vivo models.

H. N. Lode and coworkers in *PNAS USA* 96: 1591–1596 (1999) have observed synergistic effects between an antiangiogenic αv integrin antagonist and a tumor-specific antibody-cytokine (interleukin-2) fusion protein in the eradication of spontaneous tumor metastases. Their results suggested this combination as having potential for the treatment of cancer and metastatic tumor growth.

The proton ATPase which is found on the apical membrane of the osteoclast has been reported to play a significant role in the bone resorption process. Therefore, this proton pump represents an attractive target for the design of inhibitors of bone resorption which are potentially useful for the treatment and prevention of osteoporosis and related metabolic diseases (see C. Farina et al., "Selective inhibitors of the osteoclast vacuolar proton ATPase as novel bone anti-resorptive agents," *DDT*, 4: 163–172 (1999)).

Evidence has been presented that androgenic steroids play a physiological role in the development of bone mass in men and women and that androgens act directly on bone. Androgen receptors have been demonstrated in human osteoblast-like cell lines and androgens have been shown to directly stimulate bone cell proliferation and differentiation. For a discussion, reference is made to S. R. Davis, "The therapeutic use of androgens in women," *J. Steroid Biochem. Mol. Biol.*, 69: 177–184 (1999) and K. A. Hansen and S. P. T. Tho, "Androgens and Bone Health," *Seminars in Reproductive Endocrinology*," 16: 129–134 (1998). Thus, androgen receptor modulators may have utility in the treatment and prevention of bone loss in women.

Activators of the peroxisome proliferator-activated receptor-γ(PPARγ), such as the thiazolidinediones (TZD's), inhibit osteoclast-like cell formation and bone resorption in vitro. Results reported by R. Okazaki et al. in

*Endocrinology*, 140: 5060–5065 (1999) point to a local mechanism on bone marrow cells as well as a systemic one on glucose metabolism. Nonlimiting examples of PPARγ activators include troglitazone, pioglitazone, rosiglitazone, and BRL 49653.

The present invention is also directed to combinations of the compounds of the present invention with one or more agents useful in the prevention or treatment of osteoporosis. For example, the compounds of the instant invention may be effectively administered in combination with effective amounts of other agents such as an organic bisphosphonate, an estrogen receptor modulator, an androgen receptor modulator, a growth hormone secretagogue, a cathepsin K inhibitor, an HMG-CoA reductase inhibitor, a PPARγ activator, or an inhibitor of the osteoclast proton ATPase.

Additional illustrations of the invention are methods of treating tumor growth or metastasis in a mammal in need thereof, comprising administering to the mammal a therapeutically effective amount of a compound described above and one or more agents known to be cytotoxic/antiproliferative. Also, the compounds of the present invention can be administered in combination with radiation therapy for treating-cancer and metastatic tumor growth.

In addition, the integrin αvβ3 antagonist compounds of the present invention may be effectively administered in combination with a growth hormone secretagogue in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions. These diseases include: osteoporosis (including estrogen deficiency, immobilization, glucocorticoid-induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the present invention would be useful in increasing bone mass in patients with growth hormone deficiency. Thus, preferred combinations are simultaneous or alternating treatments of an αvβ3 receptor antagonist of the present invention and a growth hormone secretagogue, optionally including a third component comprising an organic bisphosphonate, preferably alendronate monosodium trihydrate.

In accordance with the method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating integrin-mediated conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixirs, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as an αvβ3 antagonist.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethylene-oxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

METHODS OF PREPARATION

Compounds of formulae I–XVI are biliary metabolites of a compound of formula (1). They are obtained in vitro by suspension in a cytochrome P450-driven bioreactor; by incubation with rat, dog, monkey, or human liver microsomes; or by incubation with rat, dog, monkey, or human hepatocytes. They can also be isolated from the bile of individuals who have ingested a compound of formula (1), using methodologies that are well-known in the art, such as reverse-phase high-performance liquid chromatography.

Illustratively, the preparation and characterization of the metabolites of compound 2 are depicted in the Schemes and described in the Examples below.

Scheme 1

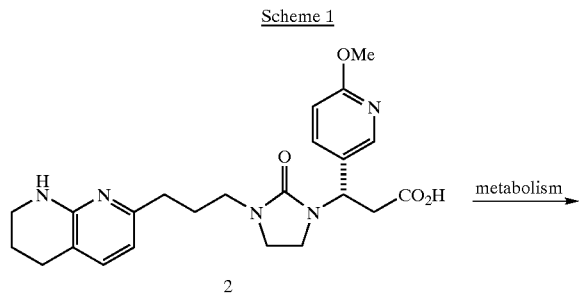

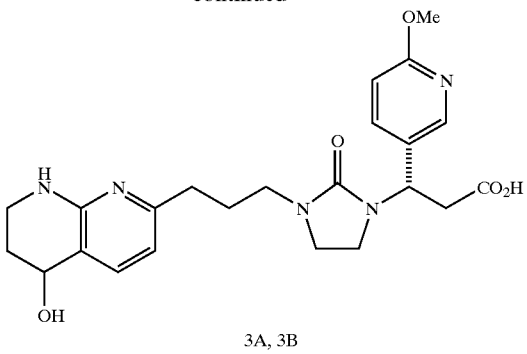

3A, 3B

EXAMPLE 1

3(S)-(6-Methoxy-pyridin-3-yl)-3-{2-oxo-3-[3-(5(R)-hydroxy-5,6,7,8-tetrahydro[1,8]naphthyridin-2-yl)-propyl]-imidazolidin-1-yl}-propionic Acid and 3(S)-(6-Methoxy-pyridin-3-yl)-3-{2-oxo-3-[3-(5(S)-hydroxy-5,6,7,8-tetrahydro[1,8]naphthyridin-2-yl)-propyl]-imidazolidin-1-yl}-propionic Acid (3A, 3B)

The bioreactor system used for the production of P450-derived metabolites has been described in "Bioreactor Systems in Drug Metabolism: Synthesis of Cytochrome P450-Generated Metabolites," T. H. Rushmore et al., *Metabolic Engineering*, 2 (2000) 1–11, which is incorporated by reference herein in its entirety.

3(S)-(6-Methoxy-pyridin-3-yl)-3-{2-oxo-3-[3-(5,6,7,8-tetrahydro[1,8]naphthyridin-2-yl)-propyl]-imidazolidin-1-yl}-propionic acid (2) (for the preparation of 2, see U.S. Pat. No. 6,017,926) (100 $\mu$M) was incubated with cells (Sf21 insect cells infected with human CYP450 2D6) in vitro at 27° C. for 24 hours. Cells were prepared by infecting with Baculovirus encoding human CYP450 2D6 or oxidoreductase and grown at 27° C. for 48 hours. The final incubation volume was 1 liter, and the CYP450 2D6 concentration was about 100 pmol/mL of cells. Incubates were centrifuged and the supernatants were first purified using a solid phase extraction column. The supernatants were loaded onto Varian Mega Bond Elut C18 (20 mL) columns, and the title compounds were eluted off the column using acetonitrile-water (1:1), and the eluant was injected onto an HPLC system for further isolation. The HPLC used in metabolite isolation was a Waters 600 HPLC system. The title compounds were separated using a Phenomenex Luna C18-2 preparative column (21.2 mm×150 mm, 5 micron). The mobile phase consisted of 0.1% formic acid in water (solvent A) and 0.1% formic acid in acetonitrile (solvent B). The eluting gradient started with an isocratic condition of 15% B for 2 min followed by a linear increase to 20% B in 10 min. The concentration of B was increased to 80% B in the next minute and the column was washed for 2 min at 80% B before returning to 15% B over 1 min. The system was equilibrated at 15% B for 10 min prior to the next injection. A constant flow rate of 20 mL/min was used for all the analyses. Under these HPLC conditions, isomer 3A eluted at about 5.5 min and isomer 3B eluted at about 6.2 min. The NMR and mass spectra of 3A and 3B were measured:

$^1$H NMR data (400 MHz, $d_6$-DMSO) for 3A and 3B: δ 8.10 (s, 1H), 7.75 (d, 1H, J=7.5 Hz), 7.70 (dd, 1H, J =8.7, 2.6 Hz); 6.82 (d, 1H, J=8.6 Hz); 6.67 (d, 1H, J=7.5 Hz), 5.20 (t, 1H, J=8.0 Hz), 4.62 (t, 1H, J=4.8 Hz), 3.82 (s, 3H), 3.41

(m, 1H), 3.29 (m, 1H), 3.20 (m, 1H), 2.92 (m, 1H), 2.97 (dd, 1H, J=15.5, 8.0 Hz), 2.87 (dd, 1H, J=15.5, 8.0 Hz), 2.59 (t, 1H, J=7.6 Hz), 1.80 (m, 1H), and 1.77 (m, 1H). Mass spectrum: found 456 (M+H)⁺; 438 (M−H₂O).

Compounds 4–9 whose structures are shown below were also identified as metabolites of substrate 2 by means of comparison of their mass and NMR spectra with those of authentic materials prepared by unambiguous chemical synthesis as depicted in Schemes 2–5 and described in Examples 2–6 below. The preparation of substrate 2 and its ethyl ester derivative 10 used as starting materials in the synthetic transformations is described in U.S. Pat. No. 6,017,926, which is incorporated by reference herein in its entirety.

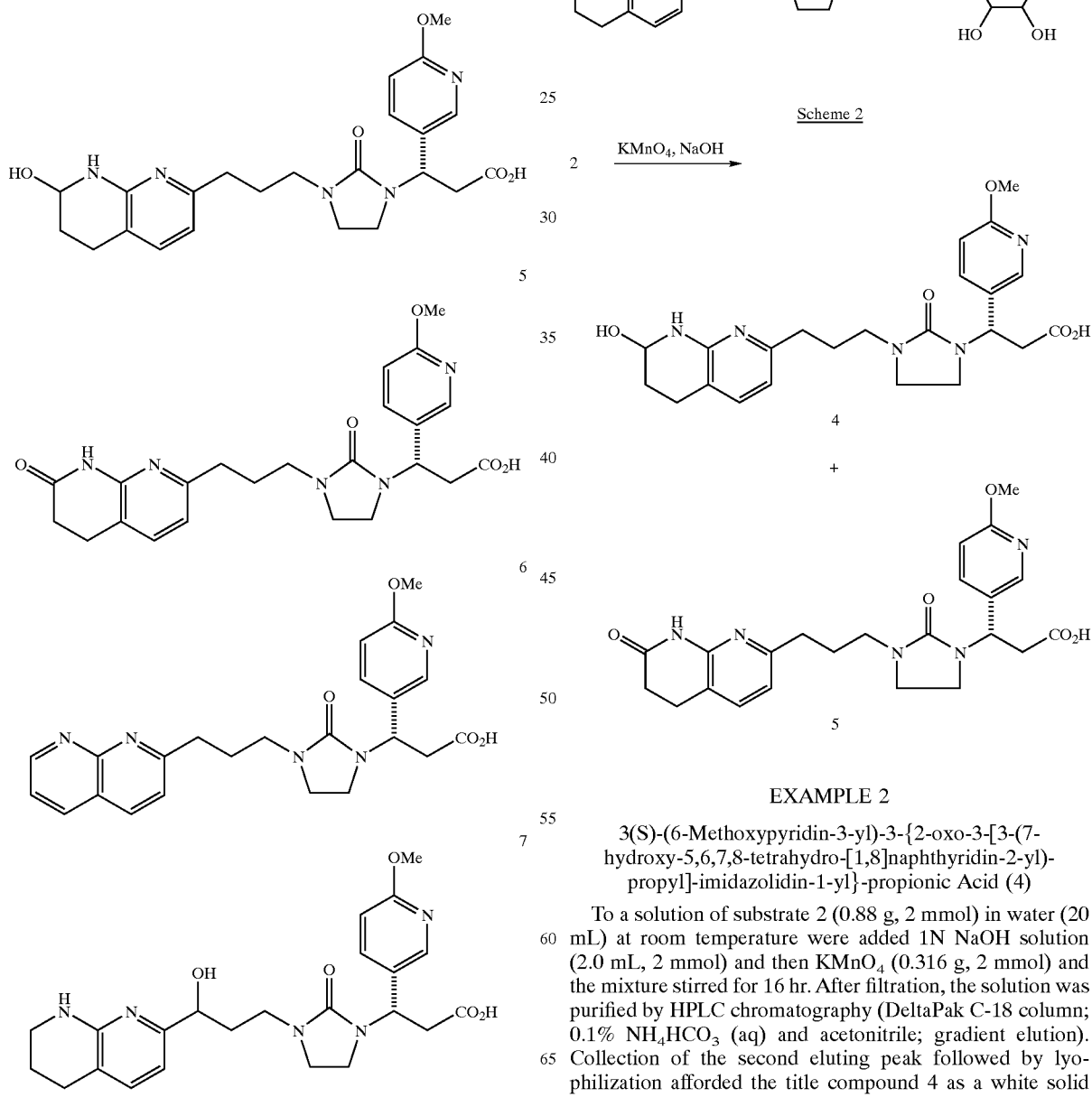

Scheme 2

EXAMPLE 2

3(S)-(6-Methoxypyridin-3-yl)-3-{2-oxo-3-[3-(7-hydroxy-5,6,7,8-tetrahydro-[1,8]naphthyridin-2-yl)-propyl]-imidazolidin-1-yl}-propionic Acid (4)

To a solution of substrate 2 (0.88 g, 2 mmol) in water (20 mL) at room temperature were added 1N NaOH solution (2.0 mL, 2 mmol) and then KMnO₄ (0.316 g, 2 mmol) and the mixture stirred for 16 hr. After filtration, the solution was purified by HPLC chromatography (DeltaPak C-18 column; 0.1% NH₄HCO₃ (aq) and acetonitrile; gradient elution). Collection of the second eluting peak followed by lyophilization afforded the title compound 4 as a white solid (1:1 mixture of 7-hydroxy epimers).

$^1$H NMR (600 MHz, CD$_3$OD): δ 1.70 (1H, m), 1.86 (1H, m), 2.07 (1H, m), 2.12 (1H, m), 2.61 (1H, m), 2.71 (2H, m), 2.75–3.0 (6H, m), 3.17 (1H, q), 3.48 (1H, m), (1H, m), 3.90 (3H, s), 4.73 (1H, m), 5.46 (1H, br d), 6.69 (1H, d), 6.80 (1H, dd), 7.54 (1H, m), 7.67 (1H, dd), 8.09 (1H, d); Mass spectrum: found 456.1 (M+H)$^+$.

EXAMPLE 3

3(S)-(6-Methoxypyridin-3-yl)-3-{2-oxo-3-[3-(7-oxo-5,6,7,8-tetrahydro-[1,8]naphthyridin-2-yl)-propyl]-imidazolidin-1-yl}-propionic Acid (5)

Following the procedure described for 4 but collecting the first eluted product following HPLC chromatography of the crude product, then concentration followed by lyophilization afforded 5 as a white solid.

$^1$H NMR (500 MHz, CD$_3$OD): δ 1.90 (2H, m), 2.57 (2H, m), 2.65 (2H, m), 2.87 (2H, m), 2.93 (3H, m), 3.13 (1H, m), 3.26 (3H, m), 3.40 (1H, q), 3.89 (3H, s), 5.37 (1H, t), 6.78 (1H, d), 6.82 (1H, d), 7.39 (1H, d), 7.67 (1H, dd), 8.11 (1H, d).; Mass spectrum: found 454.1 (M+H)$^+$.

Scheme 3

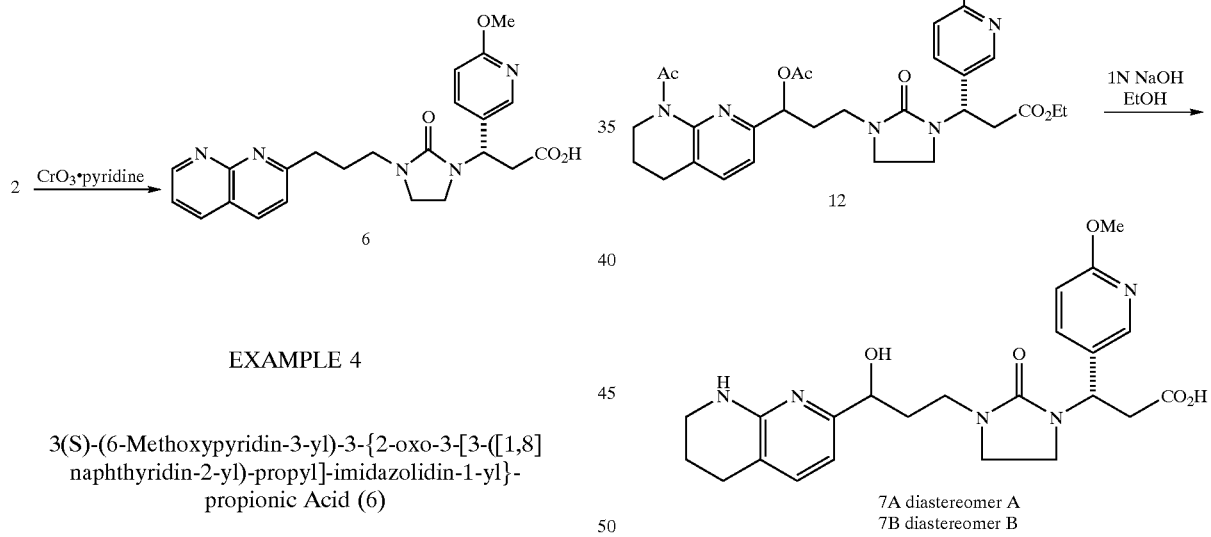

EXAMPLE 4

3(S)-(6-Methoxypyridin-3-yl)-3-{2-oxo-3-[3-([1,8]naphthyridin-2-yl)-propyl]-imidazolidin-1-yl}-propionic Acid (6)

To a solution of substrate 2 (0.44 g, 1 mmol) in pyridine (5 mL) at room temperature was added CrO$_3$ (0.1 g, 1 mmol) and the mixture stirred for 16 hr. The mixture was diluted with water (100 mL), filtered through celite and the solvent removed in vacuo to give an oil. Purification by HPLC chromatography (DeltaPak C-18 column; 0.1% NH$_4$HCO$_3$ (aq) and MeOH; gradient elution) afforded (after removal of the solvent in vacuo) a pale yellow residue. The residue was taken up in water and lyophilized to give 6 as a solid.

$^1$H NMR (300 MHz, CD$_3$OD): δ 2.12 (2H, m), 2.65–2.85 (4H, m), 3.03 (2H, t), 3.1–3.4 (4H, m), 3.75 (3H, s), 5.38 (1H, t), 6.75 (1H, d), 7.53 (1H, d), 7.57 (1H, dd), 764 (1H, dd), 8.09 (1H, d), 8.22 (1H, d), 8.36 (1H, dd), 8.98 (1H, dd); Mass spectrum: found 436.0 (M+H)$^+$.

Scheme 4

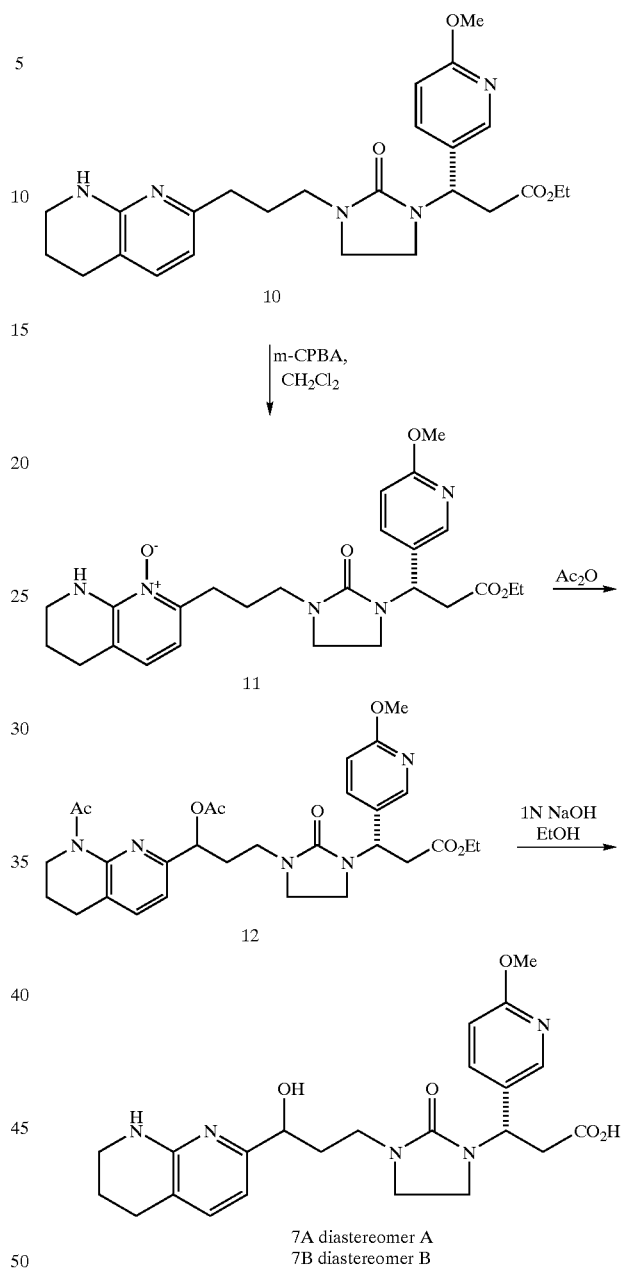

7A diastereomer A
7B diastereomer B

EXAMPLE 5

3(S)-(6-Methoxypyridin-3-yl)-3-{2-oxo-3(R or S)-[3-(5,6,7,8-tetrahydro-[1,8]naphthyridin-2-yl)-3-hydroxypropyl]-imidazolidin-1-yl}-propionic Acid Trifluoroacetic Acid Salt and 3(S)-(6-Methoxypyridin-3-yl)-3-{2-oxo-3(S or R)-[3-(5,6,7,8-tetrahydro-[1,8]naphthyridin-2-yl)-3-hydroxypropyl]-imidazolidin-1-yl}-propionic Acid Trifluoroacetic Acid Salt (7A and 7B)

Step A: 3(S)-(6-Methoxypyridin-3-yl)-3-{2-oxo-3-[3-(1N-oxide-5,6,7,8-tetrahydro-[1,8]naphthyridin-2-yl)-propyl]-imidazolidin-1-yl}-propionic Acid Ethyl Ester (11)

To a solution of the ethyl ester 10 (for preparation, see U.S. Pat. No. 6,017,926) (1.51 g, 3.2 mmol) in CH$_2$Cl$^2$ (20 mL) was added m-chloroperbenzoic acid (70%; 0.96 g, 3.9 mmol) and the mixture stirred at room temperature for 4 hours. The mixture was diluted with $CH_2Cl^2$, washed with $NaHCO_3$ (×5), brine and dried over $Na_2SO_4$. The solvent was removed and the residue purified by silica gel chromatography ($CHCl_3$/MeOH 97:3) to afford the title compound 11 as a viscous oil.

Mass spectrum: found 484.1; (M+H) calculated: 484.3.

Step B: 3(S)-(6-Methoxypyridin-3-yl)-3-{2-oxo-3-[3-(8-acetyl-5,6,7,8-tetrahydro-[1,8]naphthyridin-2-yl)-3-acetoxypropyl]-imidazolidin-1-yl}-propionic Acid Ethyl Ester (12)

A solution of the N-oxide 11 (0.24 g, 0.5 mmol) in acetic anhydride (2 mL) was heated to 90° C. for 7.5 hours then poured onto ice and neutralized with $NaHCO_3$. The mixture was extracted with EtOAc (×3), washed with brine, dried ($Na_2SO_4$) and the solvent removed. Purification of the residue by column chromatography (silica gel; $CHCl_3$/MeOH 97:3) afforded the title compound 12 as a viscous oil.

Mass spectrum: found 568.2; (M+H) calculated: 568.3.

Step C: 3(S)-(6-Methoxypyridin-3-yl)-3-{2-oxo-3(R or S)-[3-(5,6,7,8-tetrahydro-[1,8]naphthyridin-2-yl)-3-hydroxypropyl]-imidazolidin-1-yl}-propionic Acid Trifluoroacetic Acid Salt and 3(S)-(6-Methoxypyridin-3-yl)-3-{2-oxo-3(S or R)-[3-(5,6,7,8-tetrahydro-[1,8]naphthyridin-2-yl)-3-hydroxypropyl]-imidazolidin-1-yl-}-propionic Acid Trifluoroacetic Acid Salt (7A and 7B)

To a solution of the diester 12 (0.75 g, 1.32 mmol) in EtOH (10 mL) was added 1N NaOH (6 mL, 6 mmol) and the solution heated to reflux for 4 hours. The mixture was concentrated in vacuo and then purified by reverse phase HPLC (C18 column; water/acetonitrile+0.1% TFA; gradient) to give (after lyophilization) 7 as a TFA salt and mixture of diastereomers.

Mass spectrum: found 456.1; (M+H) calculated: 456.2.
$^1$H NMR (500 MHz, $CD_3OD$): δ 1.85–2.0 (4H, m), 2.82 (2H, t), 3.01 (2H, m), 3.07 (1H, m), 3.2–3.4 (4H, m), 3.44 (1H, m), 3.51 (2H, t), 3.9 (3H, s), 4.71 (1H, (1H, t), 6.71 (1H, 2 overlapping d), 6.82 (1H, 2 overlapping d), 7.61 (1H, 2 overlapping d), 7.72 (1H, 2 overlapping dd), 8.11(1H, 2 overlapping d).

The mixture of diastereomers 7 was separated by HPLC chromatography using Chiralpak AD column eluting with hexane+0.2% TFA/2-propanol/ethanol 70/25/5 to give (after lyophilization) the faster eluting diastereomer 7A as a TFA salt.

$^1$H NMR (500 MHz, $CD_3OD$): δ 1.88 (1H, septet), 1.95 (3H, m), 2.82 (2H, t), 3.01 (2H, m), 3.08 (1H, q), 3.3–3.4 (4H, m), 3.45 (1H, m), 3.51 (2H, t), 3.9 (3H, s), 4.41 (1H, dd), 5.37 (1H, t), 6.72 (1H, d), 6.82 (1H, d), 7.61 (1H, d), 7.72 (1H, dd), 8.12 (1H, d).

Continued elution afforded (after lyophilization) the slower eluting diastereomer 7B as a TFA salt.

$^1$H NMR (500 MHz, $CD_3OD$): δ 1.89 (1H, septet), 1.95 (3H, m), 2.82 (2H, t), 3.01 (2H, d), 3.07 (1H, q), 3.24 (1H, m), 3–34 (3H, m), 3.45 (1H, m), 3.51 (2H, t), 3.9 (3H, s), 4.71 (1H, dd), 5.37 (1H, t), 6.71 (1H, d), 6.82 (1H, d), 7.595 (1H, d), 7.72 (1H, dd), 8.12 (1H, d).

Scheme 5

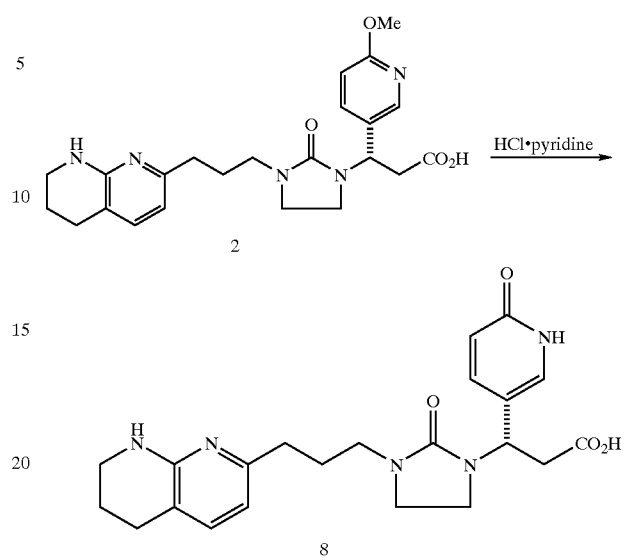

EXAMPLE 6

3(S)-(2(1H)-Pyridone-5-yl)-3-{2-oxo-3-[3-(5,6,7,8-tetrahydro-[1,8]naphthyridin-2-yl)-propyl]-imidazolidin-1-yl}-propionic Acid (8)

A mixture of the acid 2 (see U.S. Pat. No. 6,017,926; 100 mg, 0.23 mmol) and pyridine hydrochloride (300 mg) was heated in a sealed vial at 125° C. for 2.5 minutes then allowed to cool to room temperature. The residue was dissolved in water and purified by reverse phase HPLC (C-18 column; water/acetonitrile +0.1% TFA; gradient) to provide, after lyophilization, the title compound 8 as a TFA salt.

High resolution mass spectrum: found 426.2141; calculated (M+H)=426.2136. $^1$H NMR (300 MHz; $CD_3OD$): δ 1.86 (2H, m), 1.95 (1H, m), 2.66 (2H, t), 2.81 (2H, t), 2.96 (1H, m), 3.15 (1H, m), 3.23 (2H, t), 3.35–3.55 (5H, m), 5.23 (1H, t), 6.55 (1H, d), 6.64 (1H, d), 7.44 (1H, d), 7.58 (1H, d), 7.65 (1H, dd).

Assays for Determining Biological Activity:

SCHEME A
Synthesis of Radioligand for SPAV3 Assay

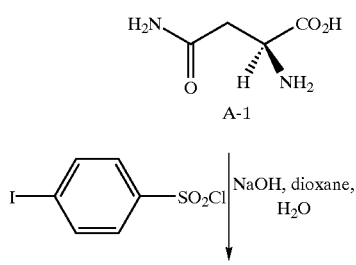

-continued
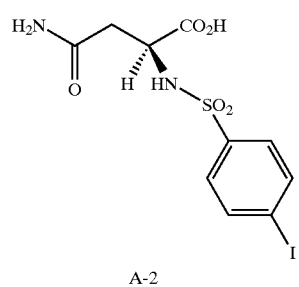
A-2
1. Br₂, NaOH, H₂O
2. HCl
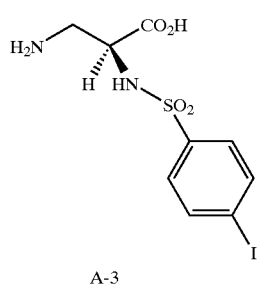
A-3
HCl
EtOH
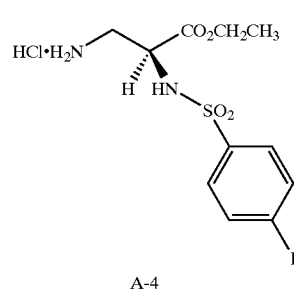
A-4
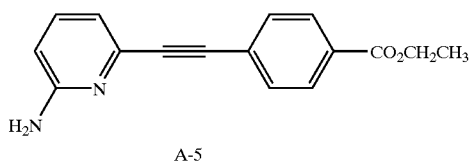
A-5
H₂,
10% Pd/C
EtOH
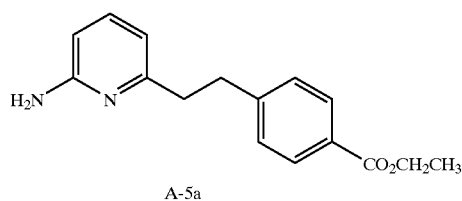
A-5a
6N HCl
-continued
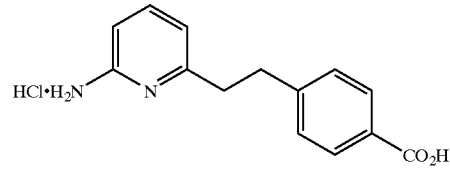
A-6
+ A-4
EDC, HOBT,
NMM, DMF
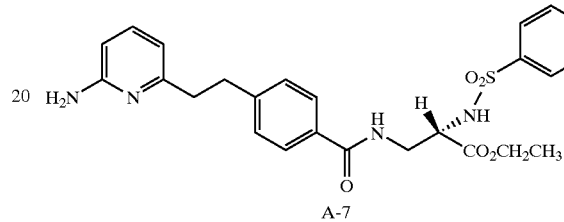
A-7
6N HCl
60° C.
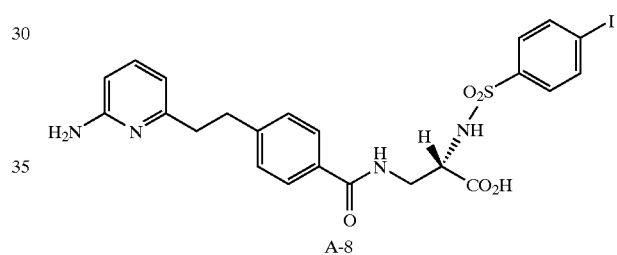
A-8
[(CH₃)₃Sn]₂, Pd(PPh₃)₄,
dioxane, 90C
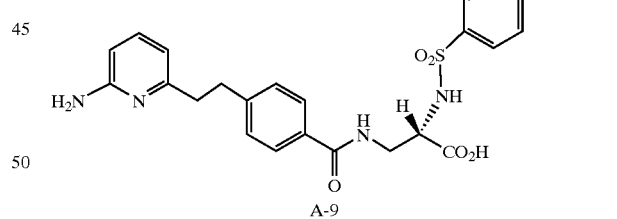
A-9
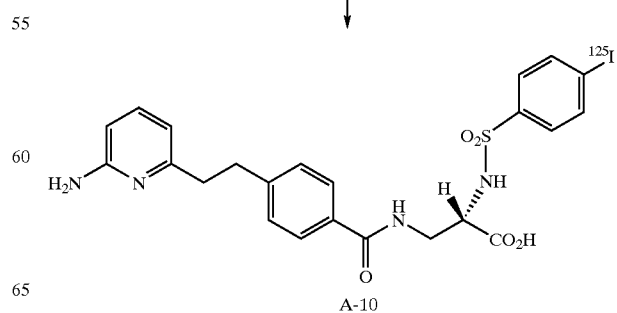
A-10

N-(4-Iodo-phenylsulfonylamino)-L-asparagine (A-2)

To stirred solution of acid A-1 (4.39 g, 3.32 mmol), NaOH (1.49 g, 37.2 mmol), dioxane (30 ml) and $H_2O$ (30 ml) at 0° C. was added pipsyl chloride (1110.34 g, 34.2 mmol). After ~5 minutes, NaOH (1.49, 37.2 mmol) dissolved in 15 ml $H_2O$, was added followed by the removal of the cooling bath. After 2.0 h, the reaction mixture was concentrated. The residue was dissolved in $H_2O$ (300 ml) and the washed with EtOAc. The aqueous portion was cooled to 0° C. and then acidified with concentrated HCl. The solid was collected and then washed with $Et_2O$ to provide acid A-2 as a white solid.

$^1$H NMR (300 MHz, $D_2O$) δ 7.86 (d, 2H, J=8 Hz), 7.48 (d, 2H, J=8 Hz) 3.70 (m, 1H, 2.39 (m, 2H).

2(S)-(4-Iodo-phenylsulfonylamino)-β-alanine (A-3)

To a stirred solution of NaOH (7.14 g, 181.8 mmol) and $H_2O$ (40 ml) at 0° C. was added $Br_2$ (1.30 ml, 24.9 mmol) dropwise over a ten minute period. After 5 minutes, acid A-2 (9.9 g, 24.9 mmol), NaOH (2.00 g, 49.8 mmol) and $H_2O$ (35 ml) were combined, cooled to 0° C. and then added in a single portion to the reaction. After stirring for 20 minutes at 0° C., the reaction was heated to 90° C. for 30 minutes and then recooled to 0° C. The pH was adjusted to ~7 by dropwise addition of concentrated HCl. The solid was collected, washed with EtOAc, and then dried in vacuo to provide acid A-3 as a white solid.

$^1$H NMR (300 MHz, $D_2O$) δ 8.02 (d, 2H, J=8 Hz), 7.63 (d, 2H, J=8 Hz), 4.36 (m, 1H), 3.51 (dd, 1H, J=5 Hz, 13 Hz) 3.21 (m, 1H).

Ethyl 2(S)-(4-Iodo-phenylsulfonylamino)-β-alanine-hydrochloride (A-4)

HCl gas was rapidly bubbled through a suspension of acid A-3 (4.0 g, 10.81 mmol) in EtOH (50 ml) at 0° C. for 10 minutes. The cooling bath was removed and the reaction was heated to 60° C. After 18 h, the reaction was concentrated to provide ester A-4 as a white solid.

$^1$H NMR (300 MHz, $CD_3OD$) δ 7.98 (d, 2H, J=8 Hz), 7.63 (d, 2H, J=8 Hz), 4.25 (q, 1H, J=5 Hz), 3.92 (m, 2H), 3.33 (m, 1H), 3.06 (m, 1H), 1.01 (t, 3H, J=7 Hz).

Ethyl 4-[2-(2-Aminopyridin-6-yl)ethyl]benzoate (A-5a)

A mixture of ester A-5 (700 mg, 2.63 mmol), (for preparation, see: Scheme 29 of PCT International Application Publication No. WO 95/32710, published Dec. 7, 1995) 10% Pd/C (350 mg) and EtOH were stirred under 1 atm $H_2$. After 20 h, the reaction was filtered through a celite pad and then concentrated to provide ester A-5a as a brown oil.

TLC $R_f$=0.23 (silica, 40% EtOAc/hexanes); $^1$H NMR (300 MHz, $CDCl_3$) δ 7.95 (d, 2H, J=8 Hz), 7.26 (m, 3H), 6.43 (d, 1H, J=7 Hz), 6.35 (d, 1H, J=8 Hz), 4.37 (m, 4H), 3.05 (m, 2H), 2.91 (m, 2H), 1.39 (t, 3H, J=7 Hz).

4-[2-(2-Aminopyridin-6-yl)ethyl]benzoic Acid Hydrochloride (A-6)

A suspension of ester A-5a (625 mg, 2.31 mmol) in 6N HCl (12 ml) was heated to 60° C. After 20 h, the reaction was concentrated to give acid A-6 as a tan solid.

$^1$H NMR (300 MHz, $CD_3OD$) δ 7.96 (d, 2H, J=8 Hz), 7.80 (m, 1H), 7.33 (d, 2H, J=8 Hz), 6.84 (d, 1H, J=9 Hz), 6.69 (d, 1H, J=7 Hz), 3.09 (m, 4H).

Ethyl 4-[2-(2-Aminopyridin-6-yl)ethyl]benzoyl-2(S)-(4-iodo-phenylsulfonylamino)-β-alanine (A-7)

A solution of acid 15-6 (400 mg, 1.43 mmol), amine A-4 (686 mg, 1.57 mmol), EDC (358 mg, 1.86 mmol), HOBT (252 mg, 1.86 mmol), NMM (632 μl, 5.72 mmol) in DMF (10 ml) was stirred for ~20 h. The reaction was diluted with EtOAc and then washed with sat. $NaHCO_3$, brine, dried ($MgSO_4$) and concentrated. Flash chromatography (silica, EtOAc then 5% isopropanol/EtOAc) provided amide A-7 as a white solid.

TLC $R_f$=0.4 (silica, 10% isopropanol/EtOAc); $^1$H NMR (300 MHz, $CD_3OD$) δ 7.79 (d, 2H, J=9 Hz) 7.61 (d, 2H, J=8 Hz), 7.52 (d, 2H, J=9 Hz), 7.29 (m, 1H), 7.27 (d, 2H, J=8 Hz), 4.20 (m, 1H), 3.95 (q, 2H, J=7 Hz), 3.66 (dd, 1H, J=6 Hz, 14 Hz), 3.49 (dd, 1H, J=8 Hz, 13 Hz), 3.01 (m, 2H), 2.86 (m, 2H, 1.08 (t, 3H, J=7 Hz).

4-[2-(2-Aminopyridin-6-yl)ethyl]benzoyl-2(S)-(4-iodophenyl-sulfonylamino)-β-alanine (A-8)

A solution of ester A-7 (200 mg, 0.3213 mmol) and 6N HCl (30 ml) was heated to 60° C. After ~20 h, the reaction mixture was concentrated. Flash chromatography (silica, 20:20:1:1 EtOAc/EtOH/$NH_4OH$/$H_2O$) provided acid A-8 as a white solid.

TLC $R_f$=0.45 (silica, 20:20:1:1 EtOAc/EtOH/$NH_4OH$/$H_2O$); $^1$H NMR (400 MHz, DMSO) δ 8.40 (m, 1H), 8.14 (Bs, 1H), 7.81 (d, 2H, J=8 Hz), 7.62 (d, 2H, J=8 Hz), 7.48 (d, 2H, J=8 Hz), 7.27 (m, 3H), 6.34 (d, 1H, J=7 Hz), 1H, J=8 Hz), 5.85 (bs, 2H), 3.89 (bs, 1H), 3.35 (m, 2H), 2.97 (m, 2H), 2.79 (m, 2H).

4-[2-(2-Aminopyridin-6-yl)ethyl)benzoyl-2(S)-(4-trimethylstannyl-phenylsulfonylamino-β-alanine (A-9)

A solution of iodide A-8 (70 mg, 0.1178 mmol), [($CH_3$)$_3$Sn]$_2$ (49 μl, 0.2356 mmol), Pd(PPh$_3$)$_4$ (5 mg) and dioxane (7 ml) was heated to 90° C. After 2 h, the reaction was concentrated and then purified by preparative HPLC (Delta-Pak $C^{18}$ 15 μM 100A°, 40×100 mm; 95:5 then 5:95 $H_2O$/$CH_3CN$) to provide the trifluoroacetate salt. The salt was suspended in $H_2O$ (10 ml), treated with $NH_4OH$ (5 drops) and then lyophilized to provide amide A-9 as a white solid.

$^1$H NMR (400 MHz, DMSO) δ 8.40 (m, 1H), 8.18 (d, 1H, J=8 Hz), 7.67 (m, 5H), 7.56 (d, 2H, J=8 Hz), 7.29 (d, 2H, J=8 Hz), 6.95–7.52 (m, 2H), 6.45 (bs, 2H), 4.00 (m, 1H), 3.50 (m, 1H), 3.33 (m, 1H), 2.97 (m, 2H), 2.86 (m, 2H).

4-[2-(2-Aminopyridin-6-yl)ethyl]benzoyl-2(S)-4-$^{125}$iodo-phenylsulfonylamino-β-alanine (A-10)

An iodobead (Pierce) was added to a shipping vial of 5 mCi of Na$^{125}$I (Amersham, IMS30) and stirred for five minutes at room temperature. A solution of 0.1 mg of A-9 in 0.05 mL of 10% $H_2SO_4$/MeOH was made and immediately added to the Na$^{125}$I/iodobead vial. After stirring for three minutes at room temperature, approximately 0.04–0.05 mL of $NH_4OH$ was added so the reaction mixture was at pH 6–7. The entire reaction mixture was injected onto the HPLC for purification [Vydac peptide-protein C-18 column, 4.6×250 mm, linear gradient of 10% acetonitrile (0.1% (TFA):$H_2O$ (0.1% TFA) to 90% acetonitrile (0.1% TFA):$H_2O$ (0.1% TFA) over 30 minutes, 1 mL/min]. The retention time of A-10 is 17 minutes under these conditions. Fractions containing the majority of the radioactivity were pooled, lyophilized and diluted with ethanol to give approximately 1 mCi of A-10, which coeluted on HPLC analysis with an authentic sample of A-8.

Instrumentation: Analytical and preparative HPLC was carried out using a Waters 600E Powerline Multi Solvent Delivery System with 0.1 mL heads with a Rheodyne 7125 injector and a Waters 990 Photodiode Array Detector with a Gilson FC203 Microfraction collector. For analytical and preparative HPLC, a Vydac peptide-protein C-18 column, 4.6×250 mm was used with a C-18 Brownlee modular guard column. The acetonitrile used for the HPLC analyses was Fisher Optima grade. The HPLC radiodetector used was a Beckman 170 Radioisotope detector. A Vydac C-18 protein and peptide column, 3.9×250 mm was used for analytical and preparative HPLC. Solutions of radioactivity were concentrated using a Speedvac vacuum centrifuge. Calibration curves and chemical concentrations were determined using a Hewlett Packard Model 8452A UV/Vis Diode Array Spectrophotometer. Sample radioactivities were determined in a Packard A5530 gamma counter.

The test procedures employed to measure αvβ3 binding and the bone resorption inhibiting activity of the compounds of the present invention are described below.

Bone Resorption pit Assay

When osteoclasts engage in bone resorption, they can cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a 6 mm cylinder of bovine femur diaphysis are cut with a low speed diamond saw (Isomet, Beuler, Ltd., Lake Bluff, Ill.). Bone slices are pooled, placed in a 10% ethanol solution and refrigerated until further use.

Prior to experimentation, bovine bone slices are ultrasonicated twice, 20 minutes each in $H_2O$. Cleaned slices are placed in 96 well plates such that two control lanes and one lane for each drug dosage are available. Each lane represents either triplicate or quadruplicate cultures. The bone slices in 96 well plates are sterilized by UV irradiation. Prior to incubation with osteoclasts, the bone slices are hydrated by the addition of 0.1 ml αMEM, pH 6.9 containing 5% fetal bovine serum and 1% penicillin/streptomycin.

Long bones from 7–14 day old rabbits (New Zealand White Hare) are dissected, cleaned of soft tissue and placed in αMEM containing 20 mM HEPES. The bones are minced using scissors until the pieces are <1 mm and transferred to a 50 ml tube in a volume of 25 ml. The tube is rocked gently by hand for 60 cycles, the tissue is sedimented for 1 min., and the supernatant is removed. Another 25 ml of medium is added to the tissue and rocked again. The second supernatant is combined with the first. The number of cells is counted excluding erythrocytes (typically ~$2\times10^7$ cells/ml). A cell suspension consisting of $5\times10^6$/ml in αMEM containing 5% fetal bovine serum, 10 nM $1,25(OH)_2D_3$, and pencillin-streptomycin is prepared. 200 ml aliquots are added to bovine bone slices (200 mm×6 mm) and incubated for 2 hrs. at 37° C. in a humidified 5% $CO_2$ atmosphere. The medium is removed gently with a micropipettor and fresh medium containing test compounds is added. The cultures are incubated for 48 hrs., and assayed for c-telopeptide (fragments of the al chain of type I collagen) by Crosslaps for culture media (Herlev, Denmark).

Bovine bone slices are exposed to osteoclasts for 20–24 hrs and are processed for staining. Tissue culture media is removed from each bone slice. Each well is washed with 200 ml of $H_2O$, and the bone slices are then fixed for 20 minutes in 2.5% glutaraldehyde, 0.1 M cacodylate, pH 7.4. After fixation, any remaining cellular debris is removed by 2 min. ultrasonication in the presence of 0.25 M $NH_4OH$ followed by 2×15 min ultrasonication in $H_2O$. The bone slices are immediately stained for 6–8 min with filtered 1% toluidine blue and 1% borax.

After the bone slices have dried, resorption pits are counted in test and control slices. Resorption pits are viewed in a Microphot Fx (Nikon) fluorescence microscope using a polarizing Nikon IGS filter cube. Test dosage results are compared with controls and resulting $IC_{50}$ values are determined for each compound tested.

The appropriateness of extrapolating data from this assay to mammalian (including human) disease states is supported by the teaching found in Sato, M., et al., *Journal of Bone and Mineral Research*, Vol. 5, No. 1, pp. 31–40, 1990, which is incorporated by reference herein in its entirety. This article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB Assay

Duong et al., *J. Bone Miner. Res.*, 8: S378 (1993), describes a system for expressing the human integrin αvβ3. It has been suggested that the integrin stimulates attachment of osteoclasts to bone matrix, since antibodies against the integrin, or RGD-containing molecules, such as echistatin (European Publication 382 451), can effectively block bone resorption.

Reaction Mixture:
1. 175 µl TBS buffer (50 mM Tris*HCl pH 7.2, 150 mM NaCl, 1% BSA, 1 mM $CaCl_2$, 1 mM $MgCl^2$).
2. 25 ml cell extract (dilute with 100 mM octylglucoside buffer to give 2000 cpm/25 µl).
3. $^{125}$I-echistatin (25 µl/50,000 cpm) (see EP 382 451).
4. 25 µl buffer (total binding) or unlabeled echistatin (non-specific binding).

The reaction mixture was then incubated for 1 h at room temp. The unbound and the bound αvβ3 were separated by filtration using a Skatron Cell Harvester. The filters (prewet in 1.5% poly-ethyleneimine for 10 mins) were then washed with the wash buffer (50 mM Tris HCl, 1 mM $CaCl^2/MgCl_2$, pH 7.2). The filter was then counted in a gamma counter.

SPAV3 Assay

Materials

1. Wheat germ agglutinin Scintillation Proximity Beads (SPA): Amersham
2. Octylglucopyranoside: Calbiochem
3. HEPES: Calbiochem
4. NaCl: Fisher
5. $CaCl^2$: Fisher
6. $MgCl_2$: SIGMA
7. Phenylmethylsulfonylfluoride (PMSF): SIGMA
8. Optiplate: PACKARD
9. Compound A-10 (specific activity 500–1000 Ci/mmole)
10. test compound
11. Purified integrin receptor: αvβ3 was purified from 293 cells overexpressing αvβ3 (Duong et a]., *J. Bone Min. Res.*, 8: S378, 1993) according to Pytela (Methods in Enzymology, 144:475, 1987)
12. Binding buffer: 50 mM HEPES, pH 7.8, 100 mM NaCl, 1 mM $Ca^{2+}/Mg^{2+}$, 0.5 mM PMSF
13. 50 mM octylglucoside in binding buffer: 50-OG buffer Procedure 1. Pretreatment of SPA beads:
   500 mg of lyophilized SPA beads were first washed four times with 200 ml of 50-OG buffer and once with 100 ml of binding buffer, and then resuspended in 12.5 ml of binding buffer.
2. Preparation of SPA beads and receptor mixture
   In each assay tube, 2.5 µl (40 mg/ml) of pretreated beads were suspended in 97.5 µl of binding buffer and 20 ml of 50-OG buffer. 5 ml (~30 ng/μl) of purified receptor was added to the beads in suspension with stirring at room temperature for 30 minutes. The mixture was then centrifuged at 2,500 rpm in a Beckman GPR Benchtop centrifuge for 10 minutes at 4° C. The pellets were then resuspended in 50 μl of binding buffer and 25 μl of 50-OG buffer.

3. Reaction

The following were sequentially added into Optiplate in corresponding wells:
(i) Receptor/beads mixture (75 μl)
(ii) 25 μl of each of the following: compound to be tested, binding buffer for total binding or A-8 for non-specific binding (final concentration 1 μM)
(iii) A-10 in binding buffer (25 μl, final concentration 40 pM)
(iv) Binding buffer (125 μl)
(v) Each plate was sealed with plate sealer from PACK-ARD and incubated overnight with rocking at 4° C.

4. Plates were counted using PACKARD TOPCOUNT % inhibition was calculated as follows:
A=total counts
B=nonspecific counts
C=sample counts
% inhibition=[{(A−B)−(C−B)}/(A−B)]/(A−B)×100

Ocform Assay

Osteoblast-like cells (1.8 cells), originally derived from mouse calvaria, were plated in CORNING 24 well tissue culture plates in αMEM medium containing ribo- and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 mL syringe with a 27.5 gauge needle. The marrow was suspended by pipetting up and down. The suspension was passed through >100 mm nylon cell strainer. The resulting suspension was centrifuged at 350×g for seven minutes. The pellet was resuspended, and a sample was diluted in 2% acetic acid to lyse the red cells. The remaining cells were counted in a hemacytometer. The cells were pelleted and resuspended at 1×10$^6$ cells/mL. 50 μl was added to each well of 1.8 cells to yield 50,000 cells/well and 1,25-dihydroxy-vitamin D$_3$ (D$_3$) was added to each well to a final concentration of 10 nM. The cultures were incubated at 37° C. in a humidified, 5% CO$_2$ atmosphere. After 48 h, the medium was changed. 72 h after the addition of bone marrow, test compounds were added with fresh medium containing D$_3$ to quadruplicate wells. Compounds were added again after 48 h with fresh medium containing D$_3$. After an additional 48 h., the medium was removed, cells were fixed with 10% formaldehyde in phosphate buffered saline for 10 minutes at room temperature, followed by a 1–2 minute treatment with ethanol:acetone (1:1) and air dried. The cells were then stained for tartrate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS-MX phosphate. After staining, the plates were washed extensively with deionized water and air dried. The number of multinucleated, positive staining cells was counted in each well.

Compounds of structural formula (I) of the present invention were tested and found to bind to human αvβ3 integrin.

These compounds were found to have IC$_{50}$ values less than 100 nM in the SPAV3 assay.

Example of a Pharmaceutical Formulation

As a specific embodiment of an oral composition, 100 mgs of Example 1 are formulated with sufficient finely divided lactose to provide a total amount of 580 to 590 mg to fill a size O hard gel capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of structural formula (I):

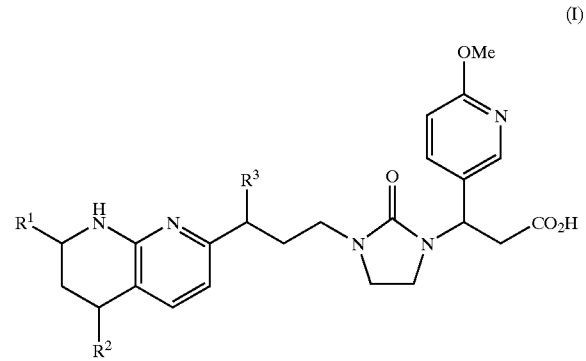

wherein at least one of $R^1$, $R^2$, and $R^3$ is hydroxy or oxo; and the individual stereoisomers thereof, or a pharmaceutically acceptable salt thereof.

2. The compound of claim 1 which is

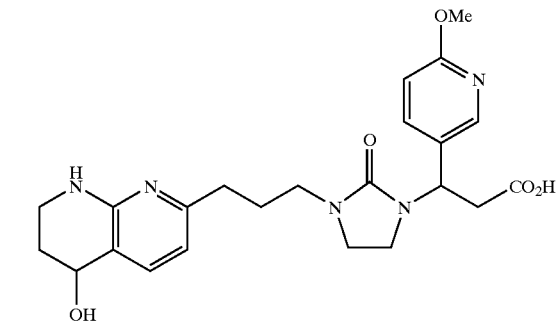

and the individual stereoisomers thereof, or a pharmaceutically acceptable salt thereof.

3. The compound of claim 2 which is

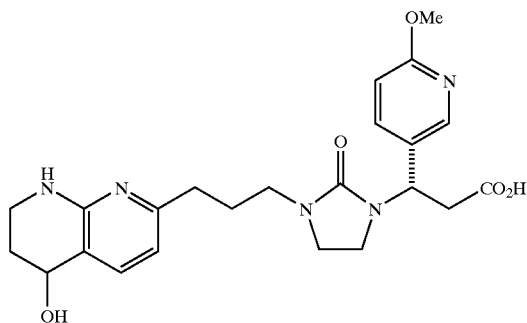

and the individual stereoisomers thereof, or a pharmaceutically acceptable salt thereof.

4. The compound of claim 1 which is (IV)

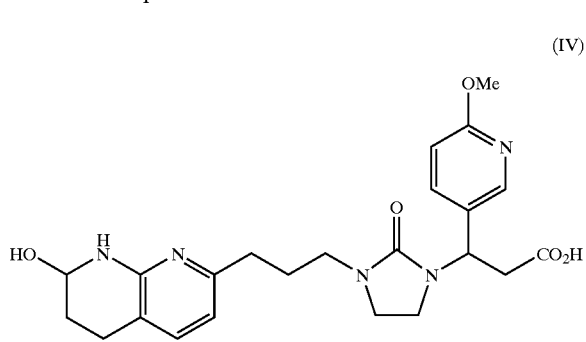

and the individual stereoisomers thereof, or a pharmaceutically acceptable salt thereof.

5. The compound of claim 4 which is

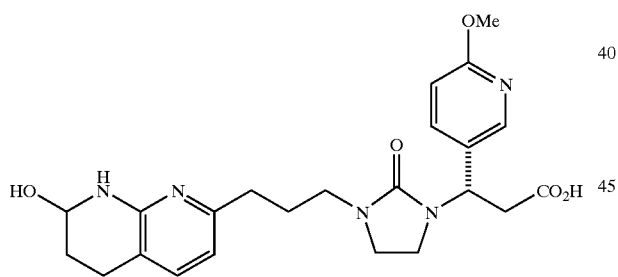

and the individual stereoisomers thereof, or a pharmaceutically acceptable salt thereof.

6. A compound of structural formula

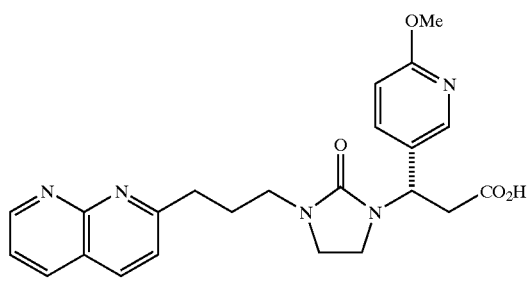

or a pharmaceutically acceptable salt thereof.

7. The compound of claim 1 which is

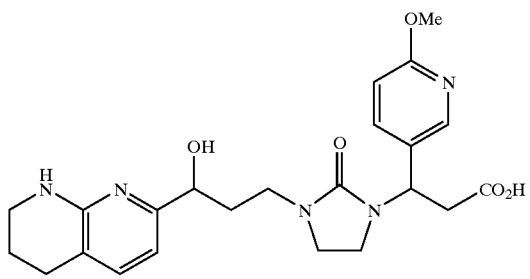

and the individual stereoisomers thereof, or a pharmaceutically acceptable salt thereof.

8. The compound of claim 7 which is

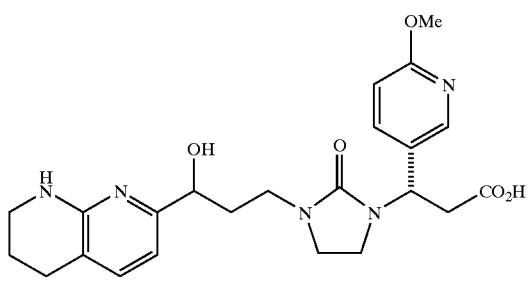

and the individual stereoisomers thereof, or a pharmaceutically acceptable salt thereof.

9. A compound of structural formula

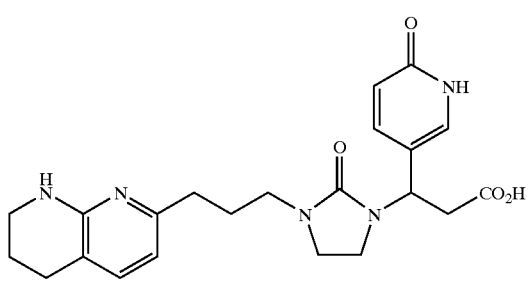

and the individual stereoisomers thereof, or a pharmaceutically acceptable salt thereof.

10. The compound of claim 9 which is

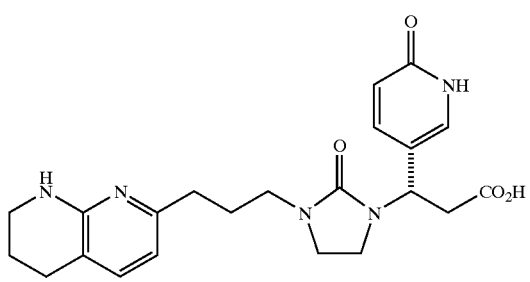

or a pharmaceutically acceptable salt thereof.

11. A pharmaceutical composition comprising a therapeutically effective amount of a compound of claim 1 and a pharmaceutically acceptable carrier.

12. A method of eliciting an αvβ3 integrin receptor antagonizing effect in a mammal in need thereof, comprising administering to said mammal a therapeutically effective amount of a compound of claim 1.

13. The method of claim 12 wherein the αvβ3 integrin receptor antagonizing effect is selected from the group consisting of inhibition of bone resorption, restenosis, angiogenesis, diabetic retinopathy, macular degeneration, inflammatory arthritis, cancer, and metastatic tumor growth.

14. The method of claim 13 wherein the αvβ3 integrin receptor antagonizing effect is inhibition of bone resorption.

15. A method of treating or preventing osteoporosis in a mammal in need thereof, comprising administering to the mammal a therapeutically effective amount of a compound of claim 1.

* * * * *